United States Patent [19]

Gross et al.

[11] Patent Number: 5,033,150
[45] Date of Patent: Jul. 23, 1991

[54] MOTOR-DRIVEN TOOTHBRUSH

[75] Inventors: Joseph Gross, Moshav Mazor; Shlomo Zucker, Yavne, both of Israel

[73] Assignee: Product Development (S.G.Z.) Ltd., Tel-Aviv, Israel

[21] Appl. No.: 471,333

[22] Filed: Jan. 29, 1990

[51] Int. Cl.⁵ .............................................. A46B 13/00
[52] U.S. Cl. ..................................... 15/22.1; 132/322
[58] Field of Search ............... 132/322, 119.1; 74/834, 74/47; 15/22.1

[56] References Cited

U.S. PATENT DOCUMENTS

| | | | |
|---|---|---|---|
| 1,506,417 | 8/1924 | Donals | 132/309 |
| 2,372,731 | 4/1945 | Nalbach et al. | 15/22.1 |
| 2,699,119 | 1/1955 | Healey | 74/834 |
| 3,029,651 | 4/1962 | Flatt | 15/22.1 |
| 3,156,936 | 11/1964 | Hartman et al. | 15/22.1 |
| 3,160,902 | 12/1964 | Aymar | 74/49 |
| 3,240,077 | 3/1966 | Smith | 74/47 |
| 4,702,428 | 10/1987 | Kempster | 74/834 |
| 4,880,382 | 11/1989 | Moret et al. | 132/309 |

Primary Examiner—Cary E. Stone
Assistant Examiner—Adriene B. Lepiane
Attorney, Agent, or Firm—Benjamin J. Barish

[57] ABSTRACT

A motor-driven toothbrush includes a housing adapted to be gripped by the user and containing an electrical rotary motor, and a toothbrush coupled to the rotary motor by an eccentric coupling such that rotation of the motor causes the toothbrush to oscillate. A sleeve threadedly received in the end of the housing through which the toothbrush handle passes defines a pivot point for the oscillations of the handle, and is adjustable with respect to the housing so as to permit varying the location of the pivot point, and thereby the type of oscillations produced by the rotary motor.

10 Claims, 1 Drawing Sheet

MOTOR-DRIVEN TOOTHBRUSH

BACKGROUND OF THE INVENTION

The present invention relates to motor-driven toothbrushes, and particularly to motor-driven toothbrushes comprising a housing adapted to be grasped by the user and containing a rotary motor, and a toothbrush coupled to the rotary motor so as to be driven thereby.

Many such motor-driven toothbrushes are known. However, efforts are continuously being made to improve the construction and operation of such toothbrushes.

OBJECTS AND SUMMARY OF THE INVENTION

An object of the present invention is to provide a motor-driven toothbrush which oscillates, rather than rotates, the toothbrush head. Another object of the invention is to provide a motor-driven toothbrush which permits the type of oscillations to be conveniently varied.

SUMMARY OF THE INVENTION

According to the present invention, there is provided a motor-driven toothbrush comprising a housing adapted to be grasped by the user and containing a rotary motor, and a toothbrush including a brush head and a handle coupled to the rotary motor so as to be driven thereby. The rotary motor is coupled to the toothbrush handle by an eccentric coupling which oscillates the handle and brush head during the rotation of the motor.

In the described preferred embodiment, the brush handle extends through an opening in the housing, such that the sides of the opening constitute a pivot point about which the toothbrush handle oscillates during the rotation of the motor. More particularly, the opening through which the handle extends is formed at one end of a sleeve, which sleeve is adjustably received at the respective end of the housing to adjust the pivot point about which the toothbrush handle oscillates during the rotation of the motor.

According to further features in the described preferred embodiment, the brush head is removably attached to the brush handle, permitting a floss holder to be attached to the handle in place of the brush head.

Further features and advantages of the invention will be apparent from the description below.

BRIEF DESCRIPTION OF THE DRAWINGS

The invention is herein described, by way of example only, with reference to the accompanying drawings, wherein.

DESCRIPTION OF A PREFERRED EMBODIMENT

Figure 1:
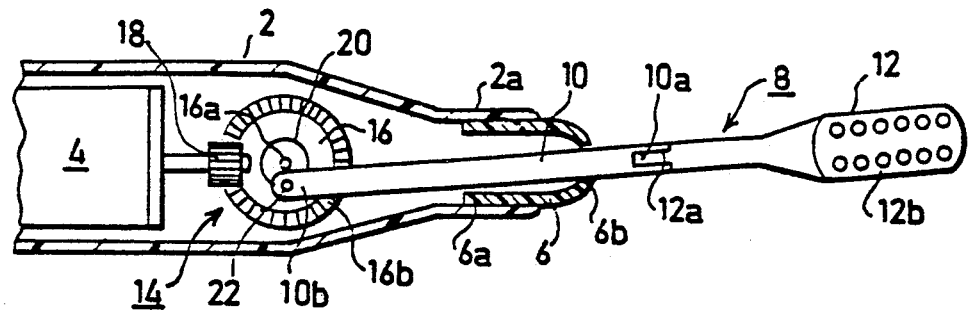
FIG. 1 is top sectional view illustrating one form of motor-driven toothbrush constructed in accordance with the present invention.
Figure 2:
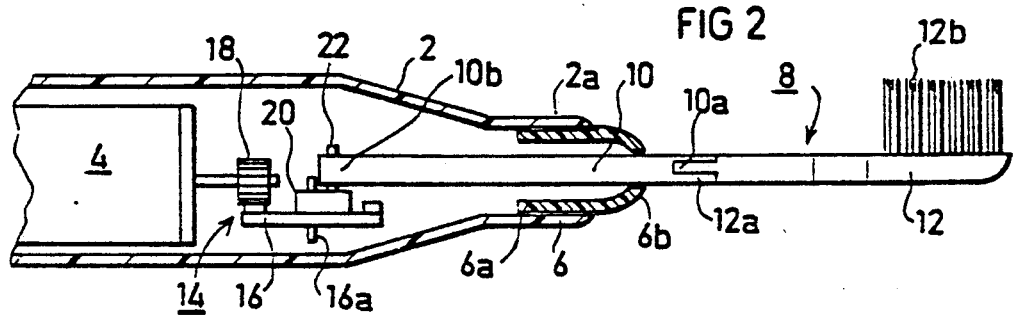
FIG. 2 is a side sectional view of the toothbrush of FIG. 1.

The toothbrush illustrated in FIGS. 1 and 2 of the drawings comprises a housing 2 adapted to be gripped by the user, and a electrical rotary motor 4 disposed within the housing. One end of the housing is open, as shown at 2a, and receives a sleeve 6. End 6a of the sleeve is of relatively large diameter and is threaded for attachment to end 2a of the housing. The opposite end of the sleeve is of reduced dimensions so that its inner surface forms an opening 6b which is substantially of the same size and rectangular configuration as a standard toothbrush handle.

A toothbrush, generally designated 8, including a handle 10 and a brush head 12, is carried by housing 2. Handle 10 is formed with a socket 10a for detachably receiving brush head 12. Brush head 12 is formed at one end as a plug 12a for reception into socket 10a of handle 10, and carries a plurality of bristles 12b at its opposite end.

The toothbrush handle 10 is passed through opening 6b of sleeve 6 and is coupled at its inner end 10b to motor 4 via an eccentric mechanism, generally designated 14, to thereby oscillate handle 10, and brush head 12 carried at is opposite end, about a fulcrum defined by the edges of opening 6b.

The eccentric mechanism 14 coupling rotary motor 4 to handle 10 comprises a ring gear 16 rotatable about its central axis 16a and formed with gear teeth 16b around its outer periphery. Ring 16 is rotated by a drive gear 18 coupled to motor 4. A disc 20 is fixed to ring gear 16 so as to be rotated with that gear, and is eccentrically coupled to the toothbrush handle 10 by a pin 22 passing through an opening in end 10b of the handle and fixed eccentrically to disc 20.

Housing 2 may also include a battery (not shown), for driving the electrical motor 4, or an electrical cord for connecting the motor to a supply mains. Housing 2 further includes an electrical switch (not shown) for controlling the energization of motor 4.

It will thus be seen that whenever motor 4 is energized, it rotates its drive gear 18, which in turn rotates the ring gear 16 and disc 20 fixed to that gear, while pin 22 coupling the toothbrush handle 10 to disc 20 oscillates the handle, and thereby the brush head 12, about the pivot point defined by opening 6b of sleeve 6. The oscillations will be in the transverse directions to the bristles 12a carried by the brush head 12, thereby causing the bristles to effectively clean the user's teeth.

It will also be seen that the pivot point for the oscillations of toothbrush handle 10 may be changed by threading sleeve 6 more or less into end 2a of the housing 2. This permits the oscillations of the brush head 12 to be varied or adjusted as may be desired for any particular case.

Figure 3:
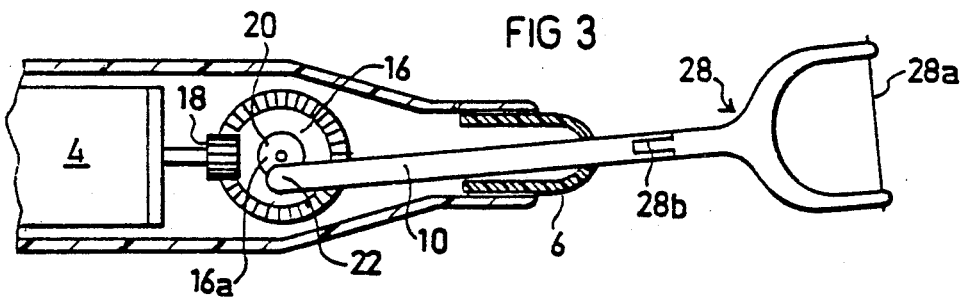
FIG. 3 is a top sectional view illustrating the toothbrush of FIG. 1 but with a floss holder substituted for the brush head.
Figure 4:
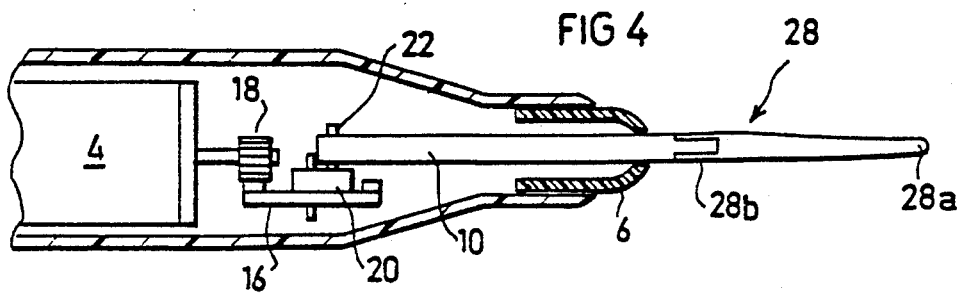
FIG. 4 is a side sectional view of the toothbrush having the floss holder of FIG. 3 mounted therein.

Socket 10a formed at the end of handle 10 permits the brush head 12 to be replaced whenever desired. In addition, it permits a floss holder, generally designated 28 in FIGS. 3 and 4, to be attached to the toothbrush handle 10 and thereby also to be oscillated by the rotation of electric motor 4. Thus, the floss holder 28 includes a piece of floss 28a extending across one end for cleaning the interdental spaces, and a plug 28b at its opposite end for insertion into socket 10a of the handle 10. When the floss holder 28 is thus attached to handle 10, rotary motor 4 will oscillate the floss 28a at the end of the holder 28 to clean the user's interdental spaces.

While the invention has been described with respect to one preferred embodiment, it will be appreciated that many variations, modifications and other applications of the invention may be made.

What is claimed is:

1. A motor-driven toothbrush, comprising: a housing including a rotary motor, said housing being formed with an opening at one end thereof;
   a sleeve attached to said housing in alignment with said opening;
   and a toothbrush including a brush head and a handle passing through said sleeve into the housing and coupled to the rotary motor via an eccentric coupling such that the rotation of the rotary motor oscillates said handle and brush head about a pivot point defined by the sides of said opening;
   said sleeve being adjustable with respect to the end of said housing to thereby adjust the pivot point about which the handle oscillates during the rotation of the motor.

2. The toothbrush according to claim 1, wherein said eccentric coupling comprises a rotary body which is rotated by said motor, and a pin passing through an opening in said toothbrush handle and eccentrically coupled to said rotary body.

3. The toothbrush according to claim 2, wherein said rotary body is in the form of a ring gear having gear teeth around its outer periphery engaged by a drive gear rotated by the motor.

4. The toothbrush according to claim 1, wherein the brush head includes a plurality of bristles extending perpendicularly to the handle, said handle and brush head being oscillated in directions transverse to said bristles.

5. The toothbrush according to claim 1, wherein said brush head is removably attached to the brush handle, permitting a floss holder to be attached to the handle in place of the brush head.

6. A motor-driven toothbrush, comprising a housing adapted to be gripped by the user and containing an electric rotary motor therein, one end of said housing being open;
   a sleeve threadedly attached at one end to said open end of the housing;
   a toothbrush including a brush head and a hand passing through an end of the sleeve opposite said one end into the housing;
   the inner dimensions of said sleeve being substantially larger than the dimensions of said handle but being reduced substantially to those of the handle at said opposite end of the sleeve, to define a pivot point for the handle;
   and an eccentric coupling coupling the end of said handle received within the housing to said rotary motor to thereby oscillate the handle and the brush head, about said pivot point defined by said sleeve;
   said sleeve being threadedly adjustable with respect to the open end of the housing to thereby vary said pivot point about which the brush handle is oscillated by the electric motor.

7. The toothbrush according to claim 6, wherein said eccentric coupling comprises a rotary body which is rotated by said motor, and a pin passing through an opening in said toothbrush handle and eccentrically coupled to said rotary body.

8. The toothbrush according to claim 7, wherein said rotary body is in the form of a ring gear having gear teeth around its outer periphery engaged by a drive gear rotated by the motor.

9. The toothbrush according to claim 6, wherein the brush head includes a plurality of bristles extending perpendicularly to the handle, said toothbrush being oscillated in directions transverse to said bristles.

10. The toothbrush according to claim 6, wherein said brush head is removably attached to the brush handle, permitting a floss holder to be attached to the handle in place of the brush head.

* * * * *